US006993437B1

(12) United States Patent
Chadwick et al.

(10) Patent No.: US 6,993,437 B1
(45) Date of Patent: Jan. 31, 2006

(54) TIDAL SEEPAGE METER

(75) Inventors: David B. Chadwick, San Diego, CA (US); Gregory Jon Groves, San Diego, CA (US); Andrew E. Patterson, Lakeside, CA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 10/790,874

(22) Filed: Mar. 2, 2004

(51) Int. Cl.
*G01F 1/00* (2006.01)
(52) U.S. Cl. .......................................... 702/45; 73/861
(58) Field of Classification Search ................. 702/45; 356/237.4; 73/863.01, 861, 863; 200/61.86; 137/625.47, 527, 884; 91/532; 251/367; 477/137
See application file for complete search history.

(56) References Cited

U.S. PATENT DOCUMENTS

| | | | | |
|---|---|---|---|---|
| 4,628,748 A | * | 12/1986 | Jogan et al. .............. | 73/863.01 |
| 5,274,434 A | * | 12/1993 | Morioka et al. ......... | 356/237.4 |
| 5,497,663 A | | 3/1996 | Reay et al. | |

OTHER PUBLICATIONS

Cherkauer, McBride, A Remotely Operated Seepage Meter for Use in Large Lakes and Rivers, vol. 26, No. 2—Mar.-Apr. 1988. p. 165-171.

* cited by examiner

*Primary Examiner*—Michael Nghiem
*Assistant Examiner*—Xiuqin Sun
(74) *Attorney, Agent, or Firm*—Allan Y. Lee; Michael A. Kagan; Peter A. Lipovsky (57) ABSTRACT

A method and apparatus for tidal seepage meters. The meter includes a power supply, controller, motor, selector valve, seepage chamber and at least two sample containers. The controller is operatively coupled to the power supply and is capable of controlling the power supply in accordance with a sampling schedule. The motor is operatively coupled to the power supply and is capable of receiving power from the power supply in accordance with the sampling schedule. The selector valve includes an input port and at least two outlet ports and is operatively coupled to the motor. The selector valve is capable of selecting an output valve in accordance with the sampling schedule. The seepage chamber is operatively coupled to the selector valve, capable of receiving seepage and inputting seepage to the selector valve via the input port. The sample containers are operatively coupled to the selector valve and receive seepage.

9 Claims, 7 Drawing Sheets

FIG. 2

DC battery to AC motor embodiment

FIG. 5
Six sample embodiment

TIDAL SEEPAGE METER

BACKGROUND OF THE INVENTION

The present invention is generally in the field of seepage meters or Lee meters. Seepage meters quantify variable rates of flow and chemical transport between groundwater and surface water.

Typical seepage meters can only obtain one sample per use, which increases cost and danger to divers when used to obtain multiple samples over a time period.

Therefore, a need exists for seepage meters that can obtain multiple samples per use.

DETAILED DESCRIPTION OF THE INVENTION

The present invention is directed to a method and apparatus for tidal seepage meters. Although the invention is described with respect to specific embodiments, the principles of the invention, as defined by the claims appended herein, can obviously be applied beyond the specifically described embodiments of the invention described herein. Moreover, in the description of the present invention, certain details have been left out in order to not obscure the inventive aspects of the invention. The details left out are within the knowledge of a person of ordinary skill in the art.

The drawings in the present application and their accompanying detailed description are directed to merely exemplary embodiments of the invention. To maintain brevity, other embodiments of the invention that use the principles of the present invention are not specifically described in the present application and are not specifically illustrated by the present drawings.

The present inventive method and apparatus for tidal seepage meters includes a power supply, controller, motor, selector valve, seepage chamber and multiple sample containers. In one embodiment, the present invention can obtain multiple samples per use.

Figure 1:
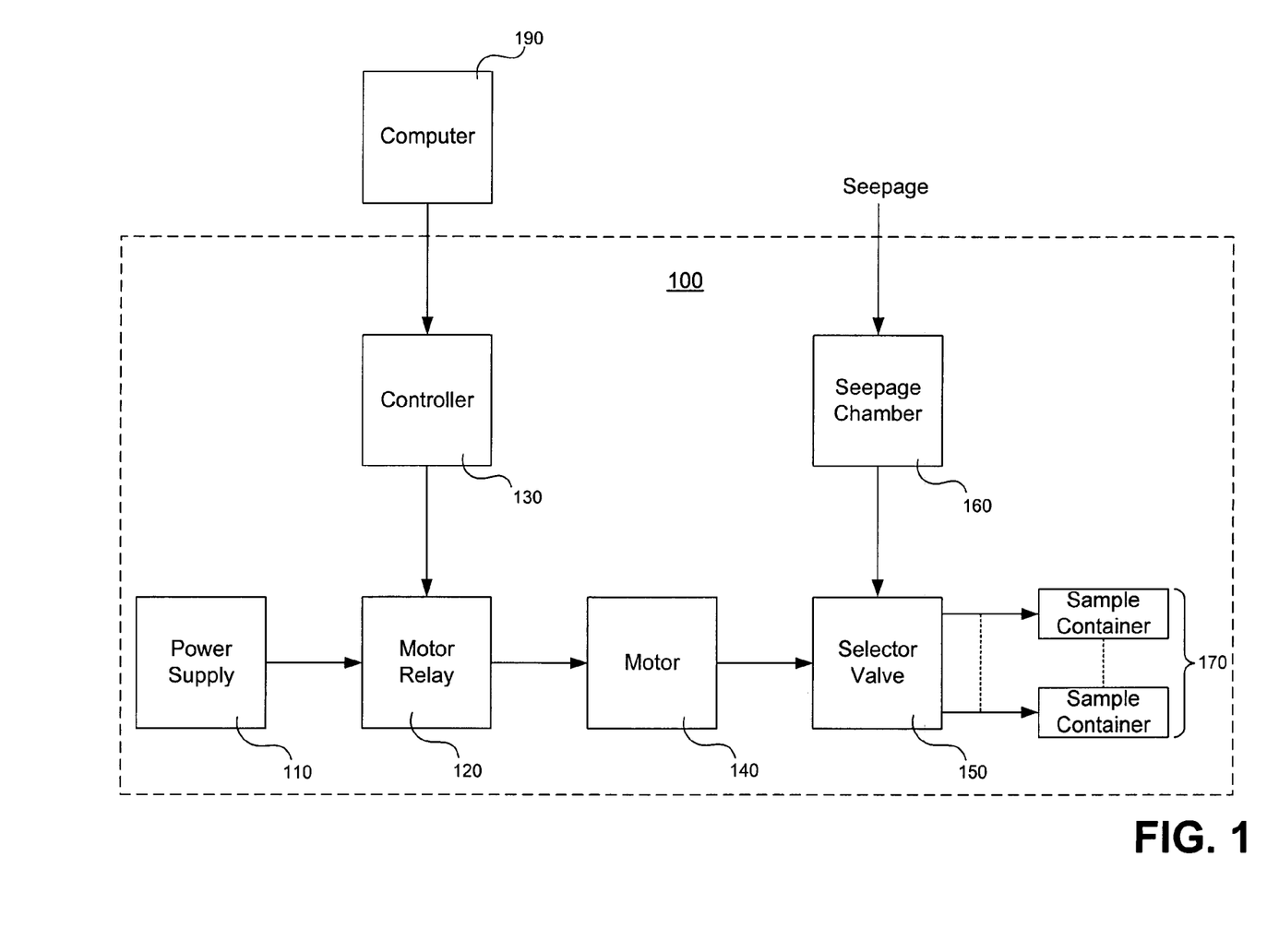
FIG. 1 is a block diagram of one embodiment of the present invention.

FIG. 1 is a block diagram of one embodiment of the present invention. As shown in FIG. 1, tidal seepage meter (TSM) 100 includes power supply 110, motor relay 120, controller 130, motor 140, selector valve 150, seepage chamber 160 and at least two sample containers 170. Controller 130 is operatively coupled to motor relay 120. Controller 130 inputs control signals to components such as motor relay 120. In one embodiment, controller 130 includes a circuit board with interpreter chip, EEPROM, 5-volt regulator, reset circuit and resonator. In one embodiment, controller 130 is a BASIC STAMP II® by PARALLAX INC. Controller 130 controls the sampling of TSM 100 according to a sampling schedule. A sampling schedule is a time schedule that designates desired times for obtaining samples. In one embodiment, a sampling schedule obtains six total samples taken at four-hour intervals, which represents a one-day tidal cycle. In one embodiment, controller 130 obtains sampling schedules from computer 190. In one embodiment, computer 190 downloads sampling schedules to controller 130 via an interface link such as six-wire cable, optical, infrared and rf links. In one embodiment, TSM 100 further includes computer 190. In one embodiment, TSM 100 temporarily links to computer 190 to receive sampling schedules. In one embodiment, controller 130 further includes an activation signal to enable/disable a power supply (e.g., power supply 110 and battery relay control signals).

Power supply 110 is operatively coupled to motor relay 120. Power supply 110 can be AC or DC power supplies. Exemplary power supplies include DC batteries and AC generators. In one embodiment, power supply 110 is a 12 VDC gel cell battery rated at 1.2 amp hour. Power supply 110 inputs voltage signals to motor relay 120.

Figure 2:
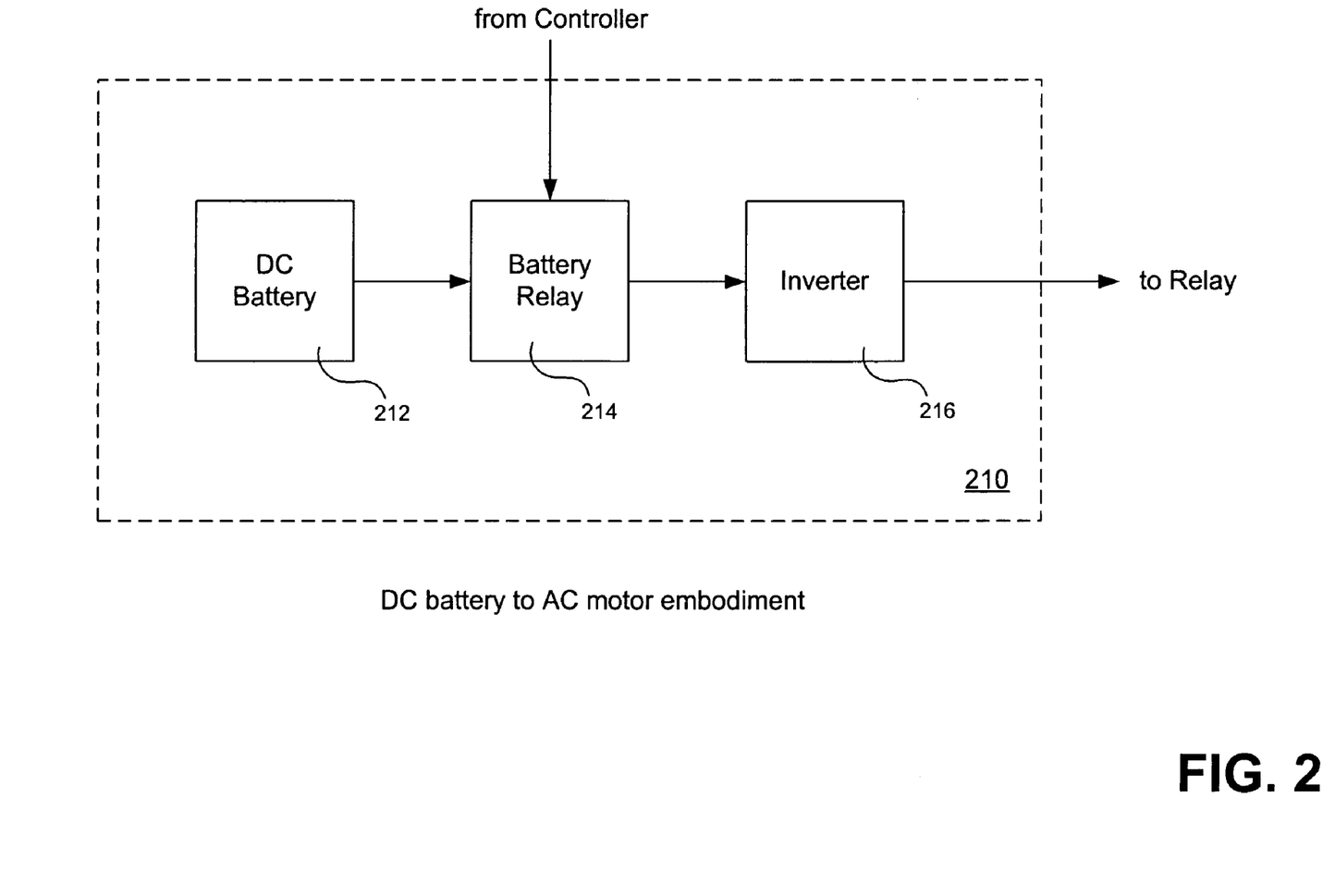
FIG. 2 is a block diagram of one embodiment of a power supply of the present invention.

FIG. 2 is a block diagram of one embodiment of a power supply of the present invention. As shown in FIG. 2, power supply 210 includes DC battery 212, battery relay 214 and inverter 216. In one embodiment, DC battery 212 is a 12 VDC gel battery rated at 1.2 amp hour. DC battery 212 is operatively coupled to battery relay 214. Battery relay 214 is capable of receiving control signals from a controller. In one embodiment, battery relay 214 is a solid state DC relay with a control line rated at 3.5–32 VDC, 1.6 microamps at 5 VDC. Battery relay 214 is operatively coupled to inverter 216. Inverter 216 is capable of inverting a DC signal to produce an AC signal. In one embodiment, inverter 216 converts 12 VDC to 115 VAC at 60 Hz. In one embodiment, inverter 216 provides 115 VAC at 140 watts. In one embodiment, inverter 216 is rated for 400-watt surges. Inverter 216 inputs an AC signal to a motor relay.

Referring again to FIG. 1, motor relay 120 is operatively coupled to power supply 110, controller 130 and motor 140. Motor relay 120 is capable of receiving control signals from controller 130. In one embodiment, motor relay 120 is a solid state AC relay with a control line rated at 3–32 VDC, 3.4 microamps at 5 VDC. Motor relay 120 operatively couples power supply 110 and motor 140 when activated by control signals from controller 130, which is in accordance with a sampling schedule.

Motor 140 is operatively coupled to motor relay 120 and selector valve 150. Motor 140 receives voltage signals from power supply 110 via motor relay 120 in accordance with a sampling schedule. Exemplary motors include stepper motors, hydraulics and spring-driven mechanisms. In one embodiment, motor 140 is an AC motor. In one embodiment, motor 140 is a DC motor. In one embodiment, motor 140 is a 90-degree stepper motor operating at 115 VAC. In one embodiment, motor 140 is a 90-degree stepper motor operating at 12 VDC. In one embodiment, motor 140 is unidirectional, NEMA 4 enclosure rated at 69 VA total power, 80 lb.-in. torque and 2 sec./90-degree rotation. Motor 140 actuates selector valve 150 when operatively coupled to power supply 110 via motor relay 120.

Seepage chamber 160 is operatively coupled to selector valve 150. Seepage chamber 160 receives seepage (i.e., water that is pushed through the interstitial spaces of marine or aquatic sediments by a hydraulic gradient formed between groundwater and offshore water levels) from sediment. Seepage chamber 160 receives seepage through an open end and outputs seepage through an outlet. In one embodiment, seepage chamber 160 is a semi-enclosed chamber (e.g., a drum cut in half having a closed end and an open end with an outlet drilled in the closed end, which is opposite of the open end). In one embodiment, seepage chamber 160 is a funnel. In one embodiment, seepage chamber 160 is a 9-inch bottom section of an 18-inch diameter SDPE container with a 2-inch threaded plug as an outlet. In one embodiment, seepage chamber 160 further comprises an outlet conduit operatively coupled to the outlet. The outlet conduit directs seepage to components such as selector valve 150. In one embodiment, the outlet conduit comprises ½-inch TEFLON® compression fitting. Seepage chamber 160 inputs seepage to selector valve 150.

Selector valve 150 is operatively coupled to motor 140, seepage chamber 160 and sample containers 170. Selector valve 150 receives seepage from seepage chamber 160. Selector valve 150 actuates via motor 140 in accordance with a sampling schedule. Selector valve 150 includes an inlet port and at least two outlet ports. In accordance with the present invention, selector valve 150 operatively couples the inlet port to one of the at least two outlet ports in accordance with a sampling schedule. In one embodiment, selector valve 150 comprises a six-way selector valve having one inlet port and six outlet ports. In one embodiment, selector valve 150 comprises a four-way selector valve having one inlet port and four outlet ports. In one embodiment, selector valve 150 comprises two four-way selector valves. In one embodiment, selector valve 150 is a ½-inch four-way selector valve comprising 316 stainless steel bar stock with TEFLON®sleeve around rotor. In one embodiment, the inlet port of selector valve 150 is operatively coupled to the outlet of the seepage chamber 160. In one embodiment, the inlet port of selector valve 150 is operatively coupled to the outlet of the seepage chamber 160 via an outlet conduit. In one embodiment, motor 140 rotates selector valve 150 90 degrees per sample time. Selector valve 150 inputs seepage to one of the plurality of sample containers 170.

Sample containers 170 are operatively coupled to selector valve 150. Sample containers 170 are vessels for containing seepage samples. Those skilled in the art shall recognize that TSM 100 can comprise multiple sample containers 170 without departing from the scope or spirit from the present invention. In one embodiment, sample containers 170 comprise TEFLON® gas sampling bags. Sample containers 170 receive seepage from seepage chamber 160 via selector valve 150. In one embodiment, a separate sample container 170 is operatively coupled to each outlet port of selector valve 150. In one embodiment, separate sample containers 170 are operatively coupled to selected outlet ports of selector valve 150.

An exemplary operation of TSM 100 is now described. Computer 190 downloads a sampling schedule to controller 130 of TSM 100. TSM 100 is positioned in sediment. Seepage enters seepage chamber 160. Controller 130 activates motor relay 120 in accordance with the sampling schedule. Motor relay 120 provides electrical coupling between power supply 110 and motor 140 when activated (e.g., activated for 2 seconds at 1400 HRS). When electrically coupled to power supply 110, motor 140 actuates selector valve 150, which selects an outlet port or, in one embodiment, a next outlet port. Seepage chamber 160 inputs seepage to an inlet port of selector valve 150. Selector valve 150 inputs seepage to one of a plurality of sample containers 170 via a selected outlet port. Controller 130 re-activates motor relay 120 in accordance with the sampling schedule to provide a desired number of samples.

Figure 3:
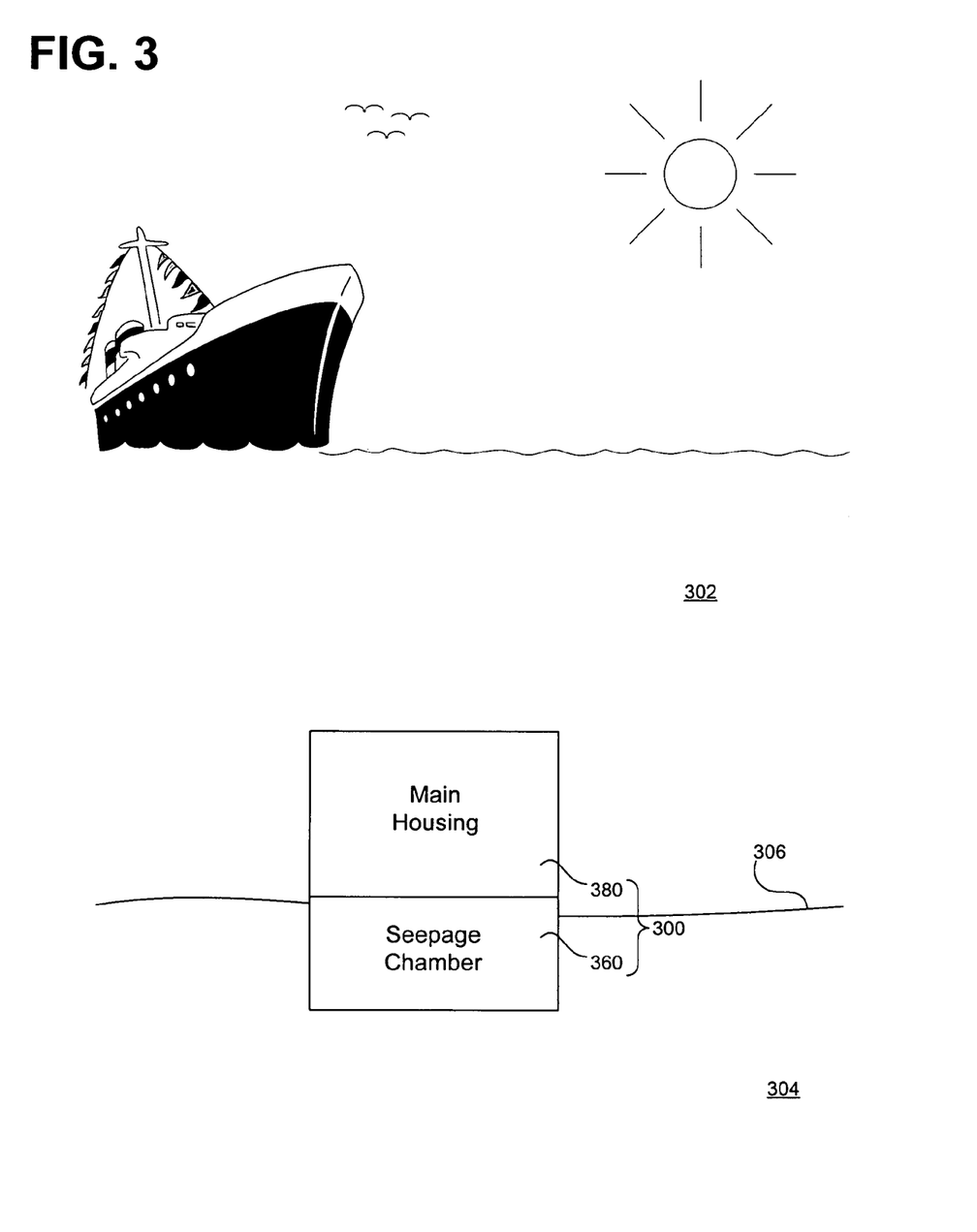
FIG. 3 is an exemplary representation of implementing an embodiment of the present invention.

FIG. 3 is an exemplary representation of an embodiment of the present invention. As shown in FIG. 3, tidal seepage meter 300 includes seepage chamber 360 and main housing 380. TSM 300 is positioned beneath water body 302 and partially embedded in sediment 304. In an exemplary implementation, TSM 300 is positioned with seepage chamber 360 substantially embedded in sediment 304 so that sediment surface 306 is substantially flush with the top of seepage chamber 360. In an exemplary implementation, one side of TSM 300 is slightly higher than other sides of TSM 300 with respect to sediment surface 306 so that seepage flows through an outlet of seepage chamber 360.

Figure 4:
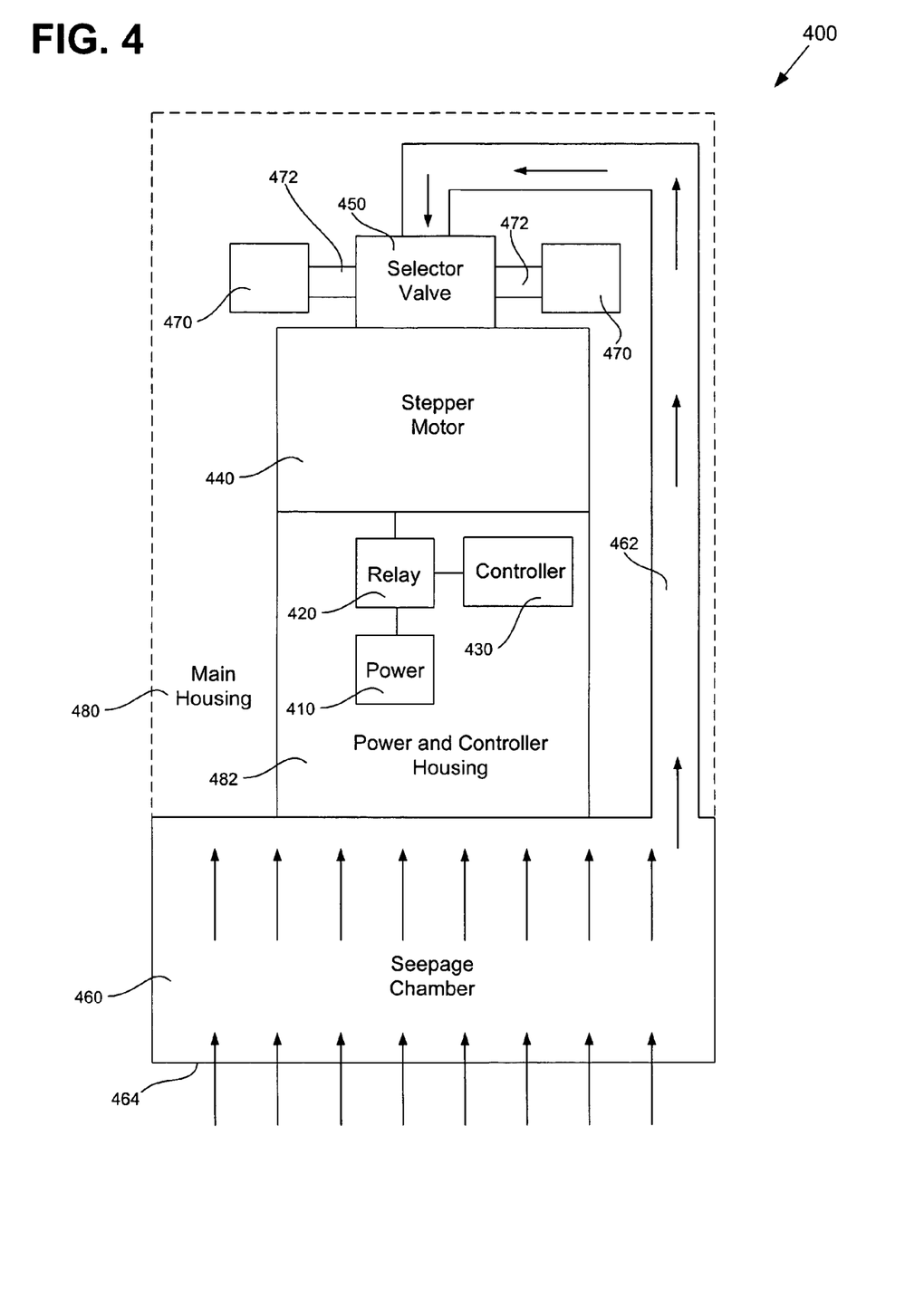
FIG. 4 is an exemplary embodiment of the present invention.

FIG. 4 is an exemplary embodiment of the present invention. As shown in FIG. 4, tidal seepage meter 400 includes seepage chamber 460, which is analogous to seepage chambers 160 and 360 of FIGS. 1 and 3, respectively, and main housing 480, which is analogous to main housing 380 of FIG. 3. TSM 400 of FIG. 4 is substantially similar to TSM 100 of FIG. 1, and thus, identical components are not described in detail hereinagain. Seepage chamber 460 further includes outlet conduit 462. Main housing 480 includes power and controller housing 482, stepper motor 440, selector valve 450 and sampling containers 470. Power and controller housing further includes power 410, relay 420 and controller 430. Selector valve 450 further comprises outlet ports 472.

Seepage chamber 460 is operatively coupled to selector valve 450 via outlet conduit 462. Seepage (represented by vertical and horizontal arrows in FIG. 4) enters seepage chamber 460 from open end 464 and travels to selector valve 450 via outlet conduit 462. Controller 430 is capable of receiving a sampling schedule. Controller 430 is operatively coupled to motor relay 420 and inputs control signals to motor relay 420 in accordance with the sampling schedule. Relay 420 operatively couples power 410 and stepper motor 440 when activated by control signals from controller 430. Stepper motor 440 actuates selector valve 450 when coupled to power 410 via relay 420. Selector valve 450 is operatively coupled to seepage chamber 460 (via outlet conduit 462), stepper motor 440 and sample containers 470 (via outlet ports 472). Selector valve 450 receives seepage from seepage chamber 460 via outlet conduit 462. Selector valve 450 directs seepage to one of the sample containers 470 via outlet ports 472. Motor 440 actuates selector valve 450 in accordance with a sampling schedule, which selects one of the plurality of sample containers 470. Although FIG. 4 shows only two sample containers, those skilled in the art shall recognize that TSM 400 can comprise more than two sample containers (e.g., six sample containers) without departing from the scope or spirit of the present invention.

Figure 5:
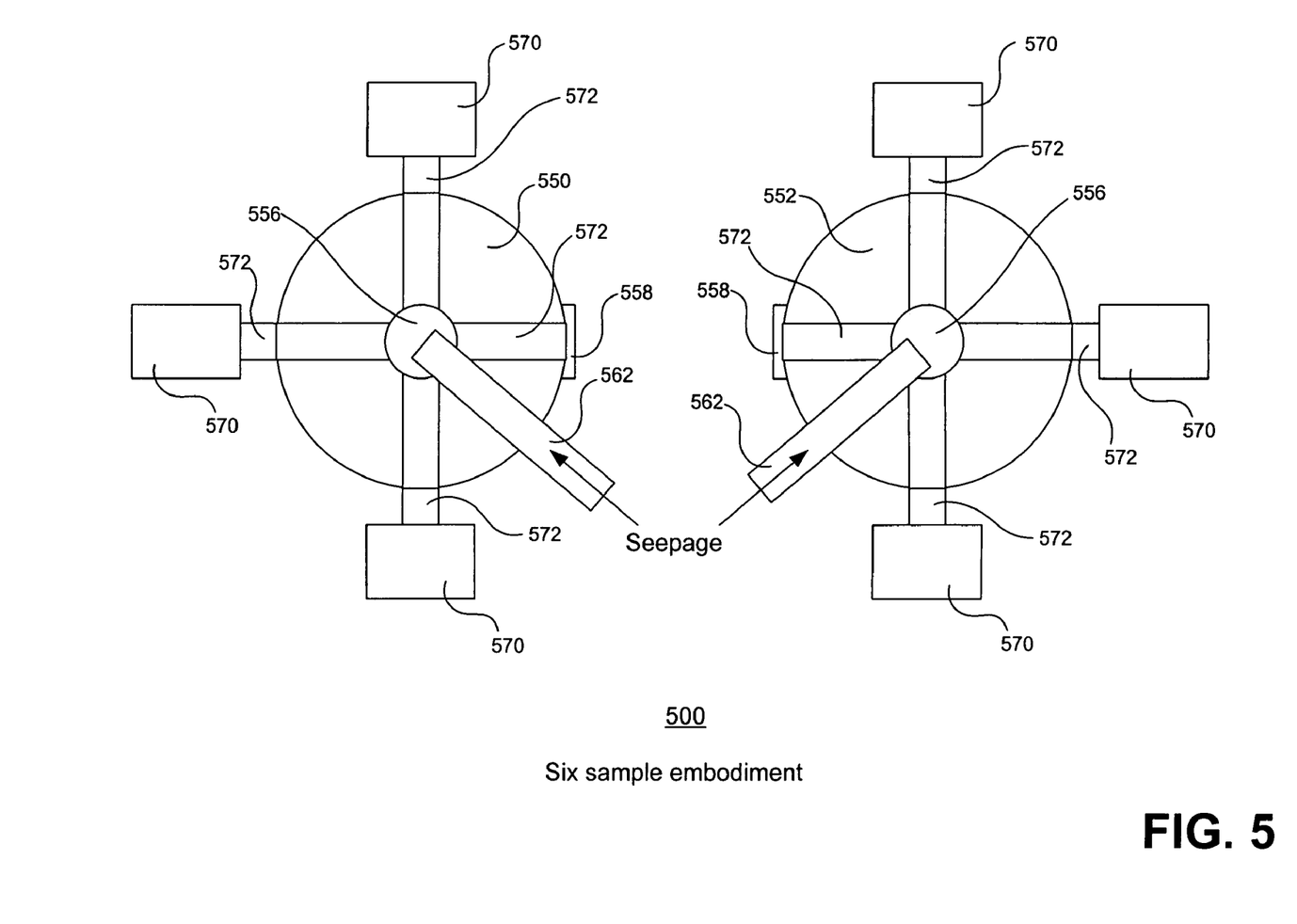
FIG. 5 is an exemplary selector valve and sample container embodiment of the present invention.

FIG. 5 is an exemplary selector valve and sample container embodiment of the present invention. The exemplary selector valve and sample container embodiment ("six-sample embodiment") 500 includes two four-way selector valves and six sample containers. As shown in FIG. 5, six-sample embodiment 500 includes selector valves 550 and 552 and sample containers 570. Inlet ports 556 of selector valves 550 and 552 receive seepage from a seepage chamber via outlet conduits 562, which are analogous to outlet conduit 462 of FIG. 4. Selector valves 550 and 552 input seepage to sample containers 570 via outlet ports 572. Stoppers 558 cover selected outlet ports of selector valves 550 and 552.

Six-sample embodiment 500 operates in the following manner. Initially, covered outlet ports of selector valves 550 and 552 are selected. Thus, seepage cannot flow out of selector valves 550 and 552. When a first sampling time occurs in accordance with a sampling schedule, a motor actuates selector valve 550, which rotates selector valve 550 90 degrees clockwise. Thus, seepage flows from outlet conduit 562 to sample container 570 located at the 6 o'clock position of selector valve 550 via inlet port 556. At a second sampling time, the motor actuates selector valve 550, which rotates selector valve 550 90 degrees clockwise. Thus, seepage flows from outlet conduit 562 to sample container 570 located at the 9 o'clock position of selector valve 550 via inlet port 556. At a third sampling time, the motor actuates selector valve 550, which rotates selector valve 550 90 degrees clockwise. Thus, seepage flows from outlet conduit 62 to sample container 570 located at the 12 o'clock position of selector valve 550 via inlet port 556. At a fourth sampling time, the motor actuates selector valve 550, which rotates selector valve 550 90 degrees clockwise, and actuates selector valve 552, which rotates selector valve 552 90 degrees clockwise. Thus, seepage is prevented from flowing out of selector valve 550 due to stopper 558; and seepage flows from outlet conduit 562 to sample container 570 located at the 12 o'clock position of selector valve 552 via inlet port 556. At a fifth sampling time, the motor actuates selector valve 552, which rotates selector valve 552 90 degrees clockwise. Thus, seepage flows from outlet conduit 562 to sample container 570 located at the 3 o'clock position of selector valve 552 via inlet port 556. At a sixth sampling time, the motor actuates selector valve 552, which rotates selector valve 552 90 degrees clockwise. Thus, seepage flows from outlet conduit 562 to sample container 570 located at the 6 o'clock position of selector valve 552 via inlet port 556. After the sixth sampling time, the motor actuates selector valve 552, which rotates selector valve 552 90 degrees clockwise. Thus, seepage is substantially prevented from flowing in outlet conduit 562 due to stopper 558 located at the 9 o'clock position of selector valve 552.

Figure 6:
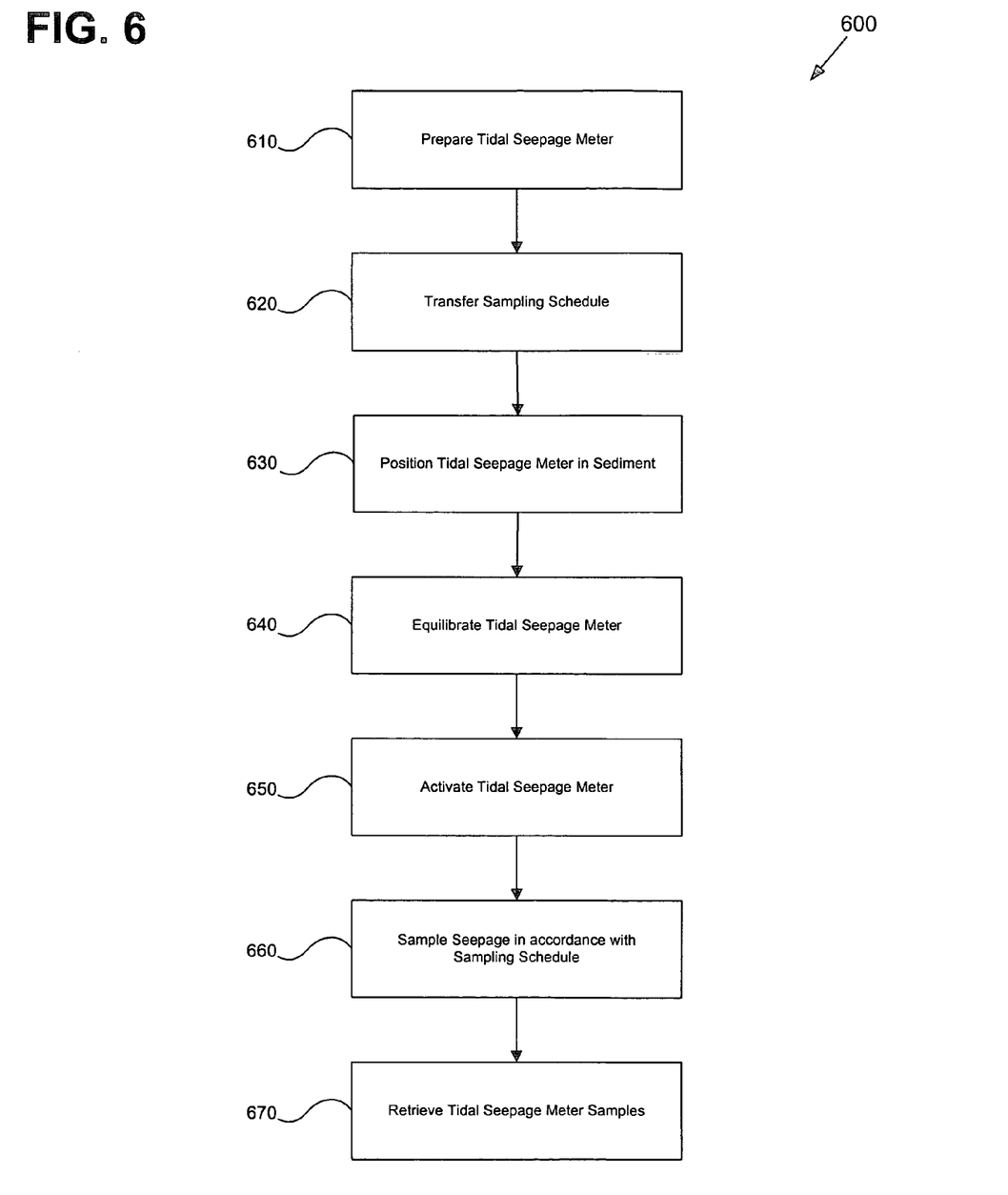
FIG. 6 is a flowchart of an exemplary method of implementing an embodiment of the present invention.

FIG. 6 is a flowchart of an exemplary method of implementing an embodiment of the present invention. Certain details and features have been left out of flowchart 600 of FIG. 6 that are apparent to a person of ordinary skill in the art. For example, a step may consist of one or more sub-steps or may involve specialized equipment or materials, as known in the art. While STEPS 610 through 670 shown in flowchart 600 are sufficient to describe one embodiment of the present invention, other embodiments of the invention may utilize steps different from those shown in flowchart 600.

Referring to FIG. 6, at STEP 610 in flowchart 600, the method prepares the tidal seepage meter. In one embodiment, the method prepares the tidal seepage meter by cleaning all plumbing. After STEP 610, the method of flowchart 600 of FIG. 6 proceeds to STEP 620.

At STEP 620 in flowchart 600, the method transfers a sampling schedule to a controller of the TSM. In one embodiment, the method downloads a sampling schedule to a controller of the TSM from a computer. After STEP 620, the method of flowchart 600 of FIG. 6 proceeds to STEP 630.

At STEP 630 in flowchart 600, the method positions the TSM in sediment. In one embodiment, the method positions the TSM in the sediment by embedding a seepage chamber of the TSM substantially in the sediment so that the sediment surface is substantially flush with the top of the seepage chamber. After STEP 630, the method of flowchart 600 of FIG. 6 proceeds to STEP 640.

At STEP 640 in flowchart 600, the method equilibrates the tidal seepage meter. In one embodiment, the method equilibrates the TSM by waiting a predetermined amount of time to allow seepage flow conditions to return to normal. After STEP 640, the method of flowchart 600 of FIG. 6 proceeds to STEP 650.

At STEP 650 in flowchart 600, the method activates the tidal seepage meter. In one embodiment, the method activates the TSM by moving a magnet mounted to the exterior of a main housing of the TSM from an "off" position to an "on" position, which activates a magnetic switch in the main housing. After STEP 650, the method of flowchart 600 of FIG. 6 proceeds to STEP 660.

At STEP 660 in flowchart 600, the method samples seepage in accordance with the sampling schedule. In one embodiment, the method sends control signals to a motor relay to operatively couple a power supply and a motor, which actuates a selector valve. The selector valve operatively couples a seepage chamber to a selected one of a plurality of sample containers. Selector valve actuation continues in accordance with the sampling schedule. After STEP 660, the method of flowchart 600 of FIG. 6 proceeds to STEP 670.

At STEP 670 in flowchart 600, the method retrieves TSM samples. In one embodiment, the method obtains TSM samples from sample containers after the TSM is retrieved.

Figure 7:
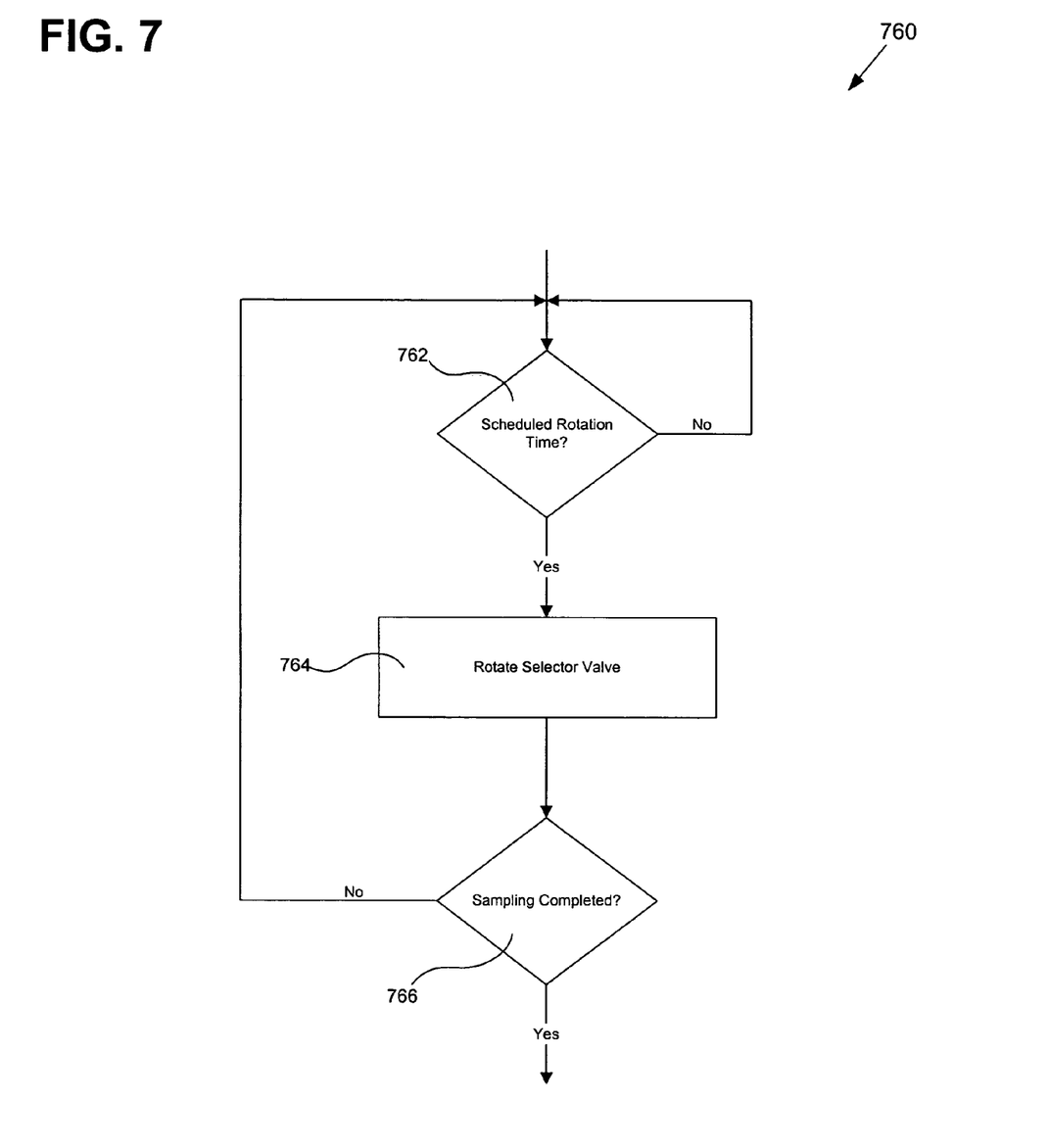
FIG. 7 is a flowchart of an exemplary method of implementing an embodiment of the present invention.

FIG. 7 is a flowchart of an exemplary method of implementing an embodiment of the present invention. Certain details and features have been left out of flowchart 760 of FIG. 7 that are apparent to a person of ordinary skill in the art. For example, a step may consist of one or more sub-steps or may involve specialized equipment or materials, as known in the art. While STEPS 762 through 766 shown in flowchart 760 are sufficient to describe one embodiment of the present invention, other embodiments of the invention may utilize steps different from those shown in flowchart 760.

Flowchart 760 is an exemplary implementation of STEP 660 of flowchart 600 of FIG. 6. Referring to FIG. 7, at decision STEP 762 in flowchart 760, the method determines whether a scheduled rotation time has occurred. If so, the method proceeds to STEP 764 whereat the method rotates a selector valve. If not, the method returns to STEP 762. After STEP 764, the method proceeds to decision STEP 766 whereat the method determines whether sampling is completed. If sampling is not completed, the method returns to decision STEP 762. If sampling is completed, the method proceeds to STEP 670 of flowchart 600 of FIG. 6. In one embodiment of STEP 766, the method rotates to a plugged port if sampling is completed and proceeds to STEP 670 of flowchart 600 of FIG. 6.

From the above description of the invention, it is manifest that various techniques can be used for implementing the concepts of the present invention without departing from its scope. Moreover, while the invention has been described with specific reference to certain embodiments, a person of ordinary skill in the art would recognize that changes can be made in form and detail without departing from the spirit and the scope of the invention. The described embodiments are to be considered in all respects as illustrative and not restrictive. It should also be understood that the invention is not limited to the particular embodiments described herein, but is capable of many rearrangements, modifications, and substitutions without departing from the scope of the invention.

We claim:

1. A tidal seepage meter, comprising:
   a) a power supply;
   b) a controller, operatively coupled to said power supply, capable of controlling said power supply in accordance with a sampling schedule;
   c) a motor, operatively coupled to said power supply, capable of receiving power from said power supply in accordance with said sampling schedule;
   d) a selector valve comprising an input port and at least two outlet ports, operatively coupled to said motor, capable of selecting an output valve in accordance with said sampling schedule;
   e) a seepage chamber, operatively coupled to said selector valve, capable of receiving seepage and inputting seepage to said selector valve via said input port;
   f) at least two sample containers, operatively coupled to said selector valve via at least two output valves, capable of receiving seepage from said selector valve via said output valve.

2. The tidal seepage meter of claim 1, wherein said controller further comprises a motor relay.

3. The tidal seepage meter of claim 1, wherein said tidal seepage meter further comprises a computer, operatively coupled to said controller.

4. The tidal seepage meter of claim 3, wherein said computer is operatively coupled to said controller during uploading of said sampling schedule.

5. The tidal seepage meter of claim 1, wherein said power supply comprises:
   i) a DC battery, capable of providing a voltage;
   ii) an inverter, operatively coupled to said motor;
   iii) a battery relay, operatively coupled to said controller, said inverter and said DC battery, capable of coupling said inverter and said DC battery in accordance with a sampling schedule.

6. The tidal seepage meter of claim 1, wherein said power supply comprises a DC battery capable of providing a voltage.

7. The tidal seepage meter of claim 1, wherein said selector valve comprises at least two multi-way selector valves.

8. The tidal seepage meter of claim 1, wherein said seepage chamber comprises a semi-enclosed chamber.

9. The tidal seepage meter of claim 1, wherein said motor comprises a stepper motor.

* * * * *